United States Patent [19]

Antoshkiw et al.

[11] 3,998,753

[45] Dec. 21, 1976

[54] WATER DISPERSIBLE CAROTENOID PREPARATIONS AND PROCESSES THEREOF

[75] Inventors: Thomas William Antoshkiw, Kearny; Marco Alfred Cannalonga, Fort Lee; Arnold Koff, West Orange, all of N.J.

[73] Assignee: Hoffmann-La Roche Inc., Nutley, N.J.

[22] Filed: Aug. 13, 1974

[21] Appl. No.: 497,025

[52] U.S. Cl. .............................. 252/312; 252/363.5; 426/250; 426/540; 426/541
[51] Int. Cl.² ..................... B01J 13/00; B01F 3/00; A23L 1/27
[58] Field of Search ...................... 252/312, 363.5; 424/171; 426/250, 540, 541, 602, 177; 8/53

[56] References Cited

UNITED STATES PATENTS 3,886,294   5/1975   Emodi .............................. 426/540

*Primary Examiner*—Samuel W. Engle
*Assistant Examiner*—Donald P. Walsh
*Attorney, Agent, or Firm*—Samuel L. Welt; Bernard S. Leon; William M. Farley

[57] ABSTRACT

This invention relates to water dispersible carotenoid compositions in liquid or powder form which are suitable for use in the preparation of colored optically clear, stable, aqueous compositions and which can be incorporated into, e.g., pharmaceutical or cosmetic preparations or animal feedstuff and to processes for their preparation.

21 Claims, No Drawings

WATER DISPERSIBLE CAROTENOID PREPARATIONS AND PROCESSES THEREOF

BACKGROUND OF THE INVENTION

Carotenoids such as carotene, lycopene, bixin, zeaxanthin, cryptoxanthin, lutein, canthaxanthin, β-apo-8'-carotenal, β-apo-12'-carotenal and esters of hydroxy- or carboxy-containing members of this group have attained considerable importance as coloring agents. This importance has increased due to possible governmental regulations withdrawing or limiting the use of certain previously certified coloring agents.

Carotenoids are yellow to red pigments either identical with or related to pigments occurring in the plant and animal kingdom. Because of this relationship to naturally occurring pigments, carotenoids possess considerable interest as replacements for the synthetic coloring agents for use as coloring materials, e.g., for foodstuffs and pharmaceutical or cosmetic properties. In addition, the carotenoids are used in animal feedstuffs to provide, for example, enhanced egg yolk or skin pigmentation as well as a source of vitamin A activity.

Carotenoids are substances which are insoluble in water and which have relatively high melting points. Moreover, carotenoids are substances which are very sensitive to oxidation. These characteristics militate against direct employment of the crystalline materials for coloration of aqueous foodstuffs or feedstuffs or for use as a source of vitamin A since in this form, the materials are poorly absorbed or give poor coloring effects. The above-mentioned characteristics of carotenoids are especially disadvantageous in the coloring of aqueous media; since, as a result of the water-insolubility of carotenoids, it is quite difficult to obtain a homogeneous or sufficiently intense color effect. Hence, the water insolubility of the carotenoids prevents their direct use as coloring agents for coloring foodstuffs having an aqueous base such as fruit juices, mineral water with fruit juices or with fruit juice flavors, ice-cream, etc. and dry products which are to be added to water in their original form or first prepared with water prior to use such as, for example, pudding powders, soup powders, powdered eggs, tomato concentrates and dry beverage bases such as lemonade powder.

SUMMARY OF THE INVENTION

This invention relates to carotenoid powder compositions which are dispersible in aqueous solutions to form optically clear aqueous compositions and which color these aqueous solutions to a desired uniform color. The carotenoid compositions can be prepared by forming a solution of a carotenoid in a volatile organic carotenoid solvent and emulsifying this solution with an aqueous solution containing sodium lauryl sulfate (SLS) using high speed mixing with high shear. The volatile solvent is then removed from the resulting emulsion by heating the emulsion while maintaining the high speed mixing with high shear until complete removal of the volatile solvent occurs. This emulsion can be used as is or it can be subsequently dried to yield carotenoid-containing powder compositons. For example, water-dispersible powders are formed by spray drying while beadlets suitable for use in animal feedstuffs are prepared by spraying droplets of the emulsion into collecting powders, e.g. starch.

DETAILED DESCRIPTION OF THE INVENTION

The carotenoids which can be used in the practice of this invention are the known natural or synthetic available representatives of this class of compounds useful as coloring agents, e.g. carotene, lycopene, bixin, zeaxanthin, cryptoxanthin, lutein, canthaxanthin, β-apo-8'-carotenal, β-apo-12'-carotenal, β-apo-8'-carotenoic acid, and esters of hydroxy- or carboxy-containing members of this group, such as lower alkyl esters and, preferably, methyl and ethyl esters. The above carotenoids can be employed singly or in admixtures, depending on the color desired. Especially preferred is canthaxanthin which either can be obtained from natural sources or prepared synthetically.

Water-dispersible powders containing from 2.5 to 15% by weight of canthaxanthin can be prepared by the process of this invention. The clarity of aqueous compositions containing these powders dispersed therein is excellent. These aqueous canthaxanthin compositions are red in color, optically clear and have marked coloring ability which is useful for the coloring of products where optical clarity is important, i.e., fruit juices, syrups, confections and the like.

Beadlets containing 1% zeaxanthin, prepared by the process of this invention, when fed to hens cause marked improvement in egg yolk pigmentation as compared to egg yolk pigmentation using a zeaxanthin of large particle size.

The quantity of sodium lauryl sulfate which is used in the emulsification process to provide optimum emulsification of the ingredients of the oil phase may vary from about 1 percent to about 6 percent by weight based on the weight of the powder composition. Higher amounts of sodium lauryl sulfate may be used without deleterious effects on the final powders but no particular advantage is achieved by the use of such higher amounts.

The carotenoid powder compositions of this invention contain, in addition to the carotenoid and sodium lauryl sulfate, from about 75% by weight to about 90 % by weight, based on the weight of the powder composition, of an edible, pharmaceutically acceptable, water-soluble carrier composition which comprises a carbohydrate, e.g., sucrose, fructose, lactose, invert sugar and the like, and a water-soluble protective colloid, e.g. gelatin, modified food starch and the like, wherein the weight ratio of water-soluble protective colloid to carbohydrate ranges from about 1/1 to about 2/1. The modified food starches are the products of the treatment of any of several grain- or root-based native starches (e.g., corn, sorghum, wheat, potato, tapioca, sago, etc.) with small amounts of certain chemical agents which modify the physical characteristics of the native starches to produce desirable properties. A preferred modified food starch for use in compositions of this invention is a starch ester—starch sodium octenyl succinate.

In addition, the carotenoid powder compositions contain from about 0.01% by weight, based on the weight of the powder composition, of an edible, pharmaceutically acceptable preservative, e.g. one or more of the following: benzoic acid, sodium benzoate, sorbic acid, potassium sorbate, methyl p-hydroxybenzoate (methylparaben), propyl p-hydroxybenzoate (propylparaben) and the like.

From about 0.05% by weight to about 0.3% by weight, based on the weight of the carotenoid powder composition, of an edible, pharmaceutically acceptable stabilizing agent, e.g. ethylene diamine tetraacetic acid (EDTA) can be used to stabilize the emulsion against the effects of trace metals.

The compositions of this invention also include from about 1% by weight to about 10% by weight, based on the weight of the carotenoid powder composition preferably from about 6% to about 7% by weight, of an edible, pharmaceutically acceptable antioxidant comprising one or more of such conventional substances as, for example, butylated hydroxyanisole (BHA), butylated hydroxytoluene (BHT), ascorbic acid and the tocoperhols. Preferred is a blend of butylated hydroxytoluene and dl-α-tocopherol used at an optimal level of about 1 part of an equal quantity of each antioxidant for 1 to 2 parts of the carotenoid.

The pH of the aqueous phase precursor of the emulsion is a critical factor since both sodium lauryl sulfate and the resulting emulsion are unstable at a pH of 7.0 or lower. In addition, spray dried carotenoid powders prepared from emulsions having these pH values of 7.0 or lower are also unstable and adversely affect the clarity of solutions prepared therefrom. Preferably, the aqueous phase emulsion precursor should be within the pH range of 10–11 with a pH of 10.4 ± 0.2 optimal. Using this aqueous phase pH range, the resulting emulsion pH after removal of chloroform and prior to spray drying can vary from about 9 to about 10. The carotenoid powders prepared from such emulsions have improved stability and form, when dispersed in aqueous food preparations or solutions, products having the optical clarity of the original uncolored products.

The modified emulsification technique employed in this invention involves the use of high-speed mixing (i.e. from about 3,000 to 12,000 rpm) coupled with a high shear force. The high shear force is essential to obtaining a small particle size for the carotenoid in the dispersed phase of the emulsion and a consequent small particle size for the carotenoid in the resulting dried carotenoid-containing powder compositions.

High shear force relates to the applied forces which cause two contiguous parts of a body to slide relative to each other in a direction parallel to their plane of contact. The effective shear force is dependent on the solids content and the viscosity of the medium being mixed, the speed of mixing and the geometry of the mixer and the mixing vessel. A type of mixer which achieves this dual function of high speed mixing and high shear force is, for example, one employing a single shaft mixer with two separated, serrated circular horizonal shear plates set between two inverted feed cones on a single shaft. Using a mixer of this type, as, for example, a Lee Turbon mixer, both high speed mixing and high shear force are rapidly achieved.

What is important in achieving the water-dispersible carotenoid powders of this invention is the obtention of a shear force high enough to keep the particle size range of the droplets of the dispersed phase below 0.1 micron in diameter. Thus, critical to the practice of this invention is the maintenance of both high speed mixing and high shear force during the removal of the volatile solvent.

The combination of both the modified emulsification technique and the use of controlled pH in conjunction with the sodium lauryl sulfate emulsifier results in a significant decrease in the particle size of the carotenoid in the dispersed oil-phase of the emulsion to below 0.1 micron and a particle size range of less than 0.1 micron for the carotenoid in the resulting dried carotenoid-containing powder compositions. This carotenoid particle size is the major factor in obtaining the optically clear, aqueous compositions upon dispersal of the carotenoid-containing powder compositions in aqueous solutions and in providing enhanced bioavailability of the carotenoid particles when used in animal feedstuffs. The particle size of the dry carotenoid-containing powder compositions is, thus, not a critical factor per se.

Thus, water-dispersible powders containing from about 2.5 to about 15% carotenoid can be prepared when sodium lauryl sulfate is used as the emulsifying agent. Clarity of the aqueous compositons prepared from these carotenoid powder compositions containing the various percentages of the carotenoids is excellent.

The volatile organic solvents suitable for use herein are those which are known solvents for the carotenoids. Such solvents include halogenated aliphatic hydrocarbons, preferably polyhalogenated methane, e.g. chloroform, carbon tetrachloride and methylene chloride. However, other volatile solvents can also be used, such as benzene or carbon disulfide. Chloroform is the preferred solvent.

In a preferred process of this invention, the aqueous phase emulsion precursor containing sodium lauryl sulfate emulsifier; a water-soluble carrier composition (gelatin, modified food starch and a sugar), preservatives (ascorbic acid, sorbic acid and sodium benzoate) and a stabilizing agent (EDTA) is prepared and the pH is adjusted to between 10–11 with a base, e.g. sodium hydroxide.

The oil phase emulsion precursor is prepared by dissolving the carotenoid and antioxidants, i.e., BHT and dl-α-tocopherol in chloroform or other suitable organic solvents. Such other suitable solvents are, as noted earlier, halogenated aliphatic hydrocarbons, benzene or carbon disulfide.

The carotenoid-containing oil phase is added to the aqueous phase using both high speed mixing and a high shear force. The high speed mixing and high shear force are continued after emulsification until all the volatile organic solvent has been removed by evaporation.

The resulting emulsion is amenable to spray drying operations using a standard spray drying tower, to drying in beadlet form by double dispersion techniques or by spraying droplets into a collecting powder, to casting of the emulsion followed by drying and comminuting, to drum drying and to lyophilization techniques.

Using the above formulations, water-dispersible carotenoid-containing powder compositions containing from 2 to about 15% by weight of the carotenoid can be prepared. The carotenoid constituent of such powder compositions have a particle size of less than 0.1 micron. The ability to form carotenoid-containing powder compositions having such a range of carotenoid concentration means, for example that quite a broad color range can be obtained in solution depending on the concentration of carotenoid in the powder.

The following examples illustrate the invention.

EXAMPLE 1

2.5% Canthaxanthin Spray-Dried Powder

330 Grams of gelatin, 279 grams of sucrose, 0.75 grams of sorbic acid and 1.50 grams of sodium benzoate are added to 330 grams of distilled water. The gelatin mixture is solubilized by hydrating overnight at about 50° C.

The following solution is prepared:

| | | |
|---|---|---|
| Ascorbic acid | 2.25 | grams |
| EDTA | 0.75 | grams |
| Sodium lauryl sulfate | 12.0 | grams |
| Distilled water | 105.0 | grams |

This solution is then added to the gelatin-sugar solution to form the aqueous phase of the emulsion. The pH of this solution is adjusted to 10.4 ± 0.2 using a 20% w/w sodium hydroxide solution.

The oil phase comprising:

| | | |
|---|---|---|
| Canthaxanthin | 23.3 | grams |
| Butylated hydroxy-toluene (BHT) | 22.5 | grams |
| dl-α-tocopherol | 22.5 | grams |
| Chloroform | 525 | grams, | is prepared by first dissolving the BHT in dl-α-tocopherol by heating the mixture to 80° C. The solution is cooled to 55° C. and then mixed with the chloroform until a clear solution results. Canthaxanthin is added to this solution under nitrogen atmosphere and dissolved.

Both the aqueous and oil phases are heated to about 50°–55° C. The oil phase is added slowly to the aqueous phase using both a high rate of mixing and a high shear force mixer. After the addition is completed, the emulsion temperature is maintained at 55° C. while high speed shear mixing is continued for 15 minutes. The temperature is gradually raised and mixing is continued until all the chloroform has been evaporated. This evaporation is usually completed when the temperature of the emulsion reaches about 75° C.

During the evaporation procedure, distilled water is added to the emulsion to maintain a suitable viscosity.

After all the chloroform has been removed sufficient distilled water is added to and thoroughly admixed with the emulsion to achieve an emulsion solids content and viscosity suitable for spray-drying.

The emulsion is spray-dried under standard spray drying conditions using a spray drying tower.

The carotenoid constituent of the resulting powder composition has a particle size which is below 0.1 micron.

The spray-dried powder is free-flowing and dissolves in water to form very clear dispersions. When used in preparations intended to be reconstituted as clear fruit flavored gelatin-type desserts and in flavored aqueous beverages, the resulting products have excellent clarity and color.

Stability, i.e. the retention of the carotenoid in the water-dispersible powder, was measured both at room temperature and at 45° C. Results are tabulated below.

| Temperature, ° C. | Time, Months | Container | % Retention |
|---|---|---|---|
| Room | 3 | Closed | 100 |
| 45 | 1 | Open | 97 |
| 45 | 1 | Closed | 100 |
| 45 | 2 | Open | 97 |
| 45 | 2 | Closed | 100 |
| 45 | 3 | Open | 94 |
| 45 | 3 | Closed | 100 |

EXAMPLE 2

The following spray-dried water-dispersible carotenoid-containing powders were formed from emulsions prepared as described in Example 1 and containing 5.0, 7.5 and 10%, of canthaxanthin:

| | 5.0% | 7.5% | 10% |
|---|---|---|---|
| Canthaxanthin | 46.6 grams | 70 grams | 93 grams |
| BHT | 22.5 grams | 22.5 grams | 22.5 grams |
| dl-α-tocopherol | 22.5 grams | 22.5 grams | 22.5 grams |
| Sucrose | 279 grams | 279 grams | 279 grams |
| Gelatin | 330 grams | 330 grams | 330 grams |
| Ascorbic acid | 2.25 grams | 2.25 grams | 2.25 grams |
| Sodium benzoate | 1.5 grams | 1.5 grams | 1.5 grams |
| Sorbic acid | 0.75 grams | 0.75 grams | 0.75 grams |
| EDTA | 0.75 grams | 0.75 grams | 0.75 grams |
| Sodium lauryl sulfate | 22 grams | 30 grams | 40 grams |
| Sodium hydroxide (20% w/w solution) to adjust pH of aqueous phase to | 10.35 | 10.4 | 10.5 |
| Final pH of emulsion | 9.65 | 9.4 | 9.4 |
| Spray dried powder, solution clarity | Very Clear | Clear | Clear |
| Gelatin dessert test* | Very Clear | Clear | Clear |
| Liquid beverage test* | Very Clear | Clear | Clear with Sl. Opalescence |

*Reconstituted

Stability data are reported below:

| Sample | Temperature, ° C. | Time, Months | Container | % Retention |
|---|---|---|---|---|
| 5% | Room | 3 | Closed | 100 |
| 5% | 45 | 1 | Open | 102 |
| 5% | 45 | 1 | Closed | 103 |
| 5% | 45 | 2 | Open | 100 |
| 5% | 45 | 2 | Closed | 103 |
| 5% | 45 | 3 | Open | 94 |
| 5% | 45 | 3 | Closed | 100 |
| 7.5% | 45 | 1 | Open | 100 |
| 7.5% | 45 | 1 | Closed | 100 |
| 10% | 45 | 1 | Open | 98 |
| 10% | 45 | 1 | Closed | 94 |

EXAMPLE 3

A water-dispersible spray-dried β-apo-8'-carotenal powder containing 5% β-apo-8'-carotenal and having the composition as listed below was prepared by spray-drying an emulsion prepared as described in Example 1.

| | |
|---|---|
| Apocartenal | 31.0 grams |
| BHT | 15.0 grams |
| dl-α-tocopherol | 15.0 grams |
| Gelatin | 135.0 grams |
| Modified Food Starch | 135.0 grams |
| Sucrose | 135.0 grams |
| Ascorbic acid | 1.5 grams |
| Sorbic acid | 0.5 grams |
| Sodium benzoate | 1.0 grams |
| EDTA | 0.5 grams |
| Sodium lauryl sulfate | 15.0 grams |
| Sodium hydroxide (20% w/w/Solution) | q.s. to aqueous phase pH of 10.4 |

EXAMPLE 4

Beadlets containing 1% zeaxanthin and having the composition listed below were prepared from an emulsion prepared as described in Example 1.

| | | |
|---|---|---|
| Zeaxanthin | 17.1 | grams |
| BHT | 22.5 | grams |
| dl-α-tocopherol | 22.5 | grams |
| Sucrose | 279 | grams |
| Gelatin | 330 | grams |
| Ascorbic acid | 2.25 | grams |
| Sodium benzoate | 1.5 | grams |
| Sorbic acid | 0.75 | grams |
| EDTA | 0.75 | grams |
| Sodium lauryl sulfate | 7.4 | grams |
| Sodium hydroxide (20% w/w solution) | q.s. to pH 10.4 | |

An apparatus provided with a revolving spray head and a counter-rotating drum was used to prepare the beadlets. In this apparatus the emulsion is forced through tiny orifices of the revolving spray head. The resulting droplets contact the powdery starch material which is suspended in air in the rotating drum. The drum and the spray head are rotated in opposite directions so that the suspension of the starchy powder in air is swirled in a direction of rotation opposite to the entering droplets of the emulsion spray.

The emulsion obtained was loaded into the revolving spray head. The drum was loaded with 2 kg. of "Dry-Flo", previously dried to a moisture content of about 3 percent. After all the emulsion had been collected in the "Dry-Flo", the mixture of starch and beadlets was allowed to stand for about an hour and then screened through a 150 mesh screen. The carotenoid-containing particles retained upon the screen were collected, spread out on drying trays and then dried in an oven.

The dry, free-flowing beadlets are suitable for use in animal feedstuff. When fed to hens, the small particle size of the zeaxanthin contained therein enhanced the yolk pigmenting effect.

We claim:

1. A process for the preparation of a water-dispersible carotenoid-containing powder wherein the carotenoid has a particle size of less than 0.1 micron which comprises the steps of
   a. forming a solution of a carotenoid and an antioxidant in a volatile organic solvent for the carotenoid, said volatile organic solvent selected from the group consisting of halogenated aliphatic hydrocarbons, benzene and carbon disulfide;
   b. forming an aqueous solution of sodium lauryl sulfate, a water-soluble carrier composition, a preservative and a stabilizer, and adjusting said solution to a pH of about 10 to 11;
   c. forming an emulsion of the solutions of steps (a) and (b) using both mixing at a high speed and high shear;
   d. removing the organic solvent while maintaining both high speed mixing and high shear;
   adjusting the solids content of the emulsion using water and
   f. spray-drying the resulting emulsion to obtain the water-dispersible, carotenoid-containing powder.

2. A water-dispersible carotenoid-containing powder prepared by the process of claim 1 using both high speed mixing and high shear wherein the carotenoid has a particle size of less than 0.1 micron comprising a carotenoid and sodium lauryl sulfate.

3. The powder of claim 2 containing, in percents by weight based on the weight of the powder, from about 2 to about 15% of a carotenoid and from about 1 to about 6% of sodium lauryl sulfate.

4. A water-dispersible carotenoid-containing powder prepared by the process of claim 1 using both high speed mixing and high shear wherein the carotenoid has a particle size of less than 0.1 micron consisting of, in percents by weight based on the weight of the powder, from about 2 to about 15% of a carotenoid, from about 1 to about 6% of sodium lauryl sulfate, from about 75 to about 90% of a pharmaceutically acceptable water-soluble carrier composition, from about 0.1 to about 0.5% of a pharmaceutically acceptable preservative, from about 0.05 to about 0.3% of a pharmaceutically stabilizing agent and from about 1 to about 10% of a pharmaceutically acceptable antioxidant.

5. The powder of claim 4 wherein the water-soluble carrier composition consists of from about 1.0 to about 2 parts of a pharmaceutically acceptable water-soluble protective colloid selected from the group consisting of gelatin and a modified food starch to one part of a carbohydrate.

6. The powder of claim 4 wherein the carotenoid is canthaxanthin.

7. The powder of claim 4 wherein the carotenoid is β-apo-8′-carotenal.

8. The powder of claim 4 wherein the carotenoid is zeaxanthin.

9. The powder of claim 4 wherein the antioxidant is a member selected from the group consisting of butylated hydroxyanisole, butylated hydroxytoluene, ascorbic acid, dl-α-tocopherol and combinations of these compounds.

10. The powder of claim 4 wherein the antioxidant consists of equal parts of butylated hydroxytoluene and dl-α-tocopherol.

11. The powder of claim 4 wherein the stabilizing agent is ethylenediamine tetraacetic acid.

12. The powder of claim 4 wherein the preservative is a member selected from the group consisting of benzoic acid, sodium benzoate, sorbic acid, methyl p-hydroxybenzoate, propyl p-hydroxybenzoate and combinations of these compounds.

13. The process of claim 1 wherein the organic solvent is removed by heating the emulsion while maintaining highspeed, high shear mixing.

14. The process of claim 1 wherein the carotenoid is canthaxanthin.

15. The process of claim 1 wherein the carotenoid is β-apo-8′-carotenal.

16. The process of claim 1 wherein the carotenoid is zeaxanthin.

17. The process of claim 1 wherein the water soluble carrier composition consists of from about 1 to about 2 parts of a pharmaceutically acceptable, water-soluble protective colloid selected from the group consisting of gelatin and a modified food starch to one part of a carbohydrate.

18. The process of claim 1 wherein the volatile organic solvent for the carotenoid is chloroform.

19. A process for the preparation of an aqueous emulsion wherein the carotenoid component in the dispersed oil phase has a particle size of less than 0.1 micron which comprises the steps of:
   a. forming a solution of a carotenoid and an antioxidant in a volatile organic solvent for the carotenoid, said volatile organic solvent selected from the group consisting of halogenated aliphatic hydrocarbons, benzene and carbon disulfide;
   b. forming an aqueous solution of sodium lauryl sulfate, a water-soluble carrier composition, a preservative and a stabilizer, and adjusting said solution to a pH of about 10 to 11;
   c. forming an emulsion of the solutions of steps (a) and (b) using both mixing at a high speed and high shear and
   d. removing the organic solvent while maintaining both high speed mixing and high shear to obtain the carotenoid component in the aforesaid particle size.

20. A process for the preparation of carotenoid-containing beadlets wherein the carotenoid has a particle size of less than 0.1 micron which comprises following steps
   (a) – (d) of claim 19 and
   e. forming the emulsion into droplets;
   f. collecting the droplets in a powdery starch material,
   g. separating the carotenoid-containing particles from the powdery starch material and
   h. drying the carotenoid-containing particles to obtain the aforesaid beadlets.

21. The process of claim 19 wherein the volatile organic solvent for the carotenoid is chloroform.

* * * * *